US008377462B2

(12) United States Patent
DesNoyer et al.

(10) Patent No.: US 8,377,462 B2
(45) Date of Patent: *Feb. 19, 2013

(54) PEA-TEMPO/PEA-BZ COATINGS FOR CONTROLLED DELIVERY OF DRUG FROM IMPLANTABLE MEDICAL DEVICES

(75) Inventors: Jessica Reneé DesNoyer, San Jose, CA (US); Lothar Walter Kleiner, Los Altos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1326 days.

This patent is subject to a terminal disclaimer.

(21) Appl. No.: 11/192,624

(22) Filed: Jul. 29, 2005

(65) Prior Publication Data

US 2007/0026041 A1    Feb. 1, 2007

(51) Int. Cl.
*A61K 31/4745* (2006.01)
*A61F 2/00* (2006.01)

(52) U.S. Cl. .................. 424/426; 424/423; 514/291

(58) Field of Classification Search .................. None
See application file for complete search history.

(56) References Cited

U.S. PATENT DOCUMENTS

| | | | |
|---|---|---|---|
| 4,304,767 A | 12/1981 | Heller et al. | |
| 4,733,665 A | 3/1988 | Palmaz | |
| 4,800,882 A | 1/1989 | Gianturco | |
| 4,886,062 A | 12/1989 | Wiktor | |
| 5,581,387 A | 12/1996 | Cahill | |
| 5,824,048 A * | 10/1998 | Tuch ............................. | 128/898 |
| 5,861,387 A | 1/1999 | Labrie et al. | |
| 6,503,538 B1 * | 1/2003 | Chu et al. ....................... | 424/497 |
| 6,703,040 B2 | 3/2004 | Katsarava et al. | |
| 7,056,591 B1 | 6/2006 | Pacetti et al. | |
| 7,166,680 B2 | 1/2007 | DesNoyer et al. | |
| 7,202,325 B2 | 4/2007 | Hossainy et al. | |
| 7,220,816 B2 | 5/2007 | Pacetti et al. | |
| 7,390,497 B2 | 6/2008 | DesNoyer et al. | |
| 7,419,504 B2 | 9/2008 | Hossainy | |
| 7,435,788 B2 | 10/2008 | Pacetti et al. | |
| 2004/0170685 A1 * | 9/2004 | Carpenter et al. ............. | 424/468 |
| 2005/0004158 A1 * | 1/2005 | Iyer et al. ....................... | 514/291 |
| 2005/0106204 A1 | 5/2005 | Hossainy et al. | |
| 2005/0112171 A1 | 5/2005 | Tang et al. | |
| 2005/0208091 A1 | 9/2005 | Pacetti | |
| 2005/0245637 A1 | 11/2005 | Tang et al. | |
| 2005/0265960 A1 | 12/2005 | Pacetti et al. | |
| 2005/0271700 A1 | 12/2005 | DesNoyer et al. | |
| 2006/0002977 A1 * | 1/2006 | Dugan .......................... | 424/426 |
| 2006/0074191 A1 * | 4/2006 | DesNoyer et al. ............. | 525/178 |
| 2006/0089485 A1 | 4/2006 | DesNoyer et al. | |
| 2006/0115513 A1 * | 6/2006 | Hossainy et al. ............. | 424/423 |
| 2006/0136048 A1 * | 6/2006 | Pacetti et al. ................. | 623/1.42 |
| 2006/0147412 A1 | 7/2006 | Hossainy et al. | |

OTHER PUBLICATIONS

Grube and Buellesfeld, 2004. Rapamycin analogs for stent-based local drug delivery. Herz, vol. 29, pp. 162-166.*
Casscells et al, 1994. Mechanisms of restenosis. Molecular and Cellular Cardiology, vol. 21(1):68-77.*
Chen and Fujise, 2005. Restenosis: Emerging molecular targets; Going beyond drug-eluting stents. Drug Discovery Today: Disease Mechanisms, vol. 2(1):1-9.*
Bauters et al, 1996. Mechanisms and prevention of restenosis: from experimental models to clinical. Cardiovascular Research, vol. 31:835-846.*
Kastrati et al, 2005. Sirolimus-eluting stent or paclitaxel-eluting stent vs. balloon angioplasty for prevention of recurrences in patients with coronary in-stent restenosis: A randomized controlled trial. JAMA, vol. 293(2):165-171.*
Lefkovits and Topol, 1997. Pharmacological approaches for the prevention of restenosis after percutaneous coronary intervention. Progress in Cardiovascular Diseases, vol. 40(2):141-158.*
Losordo et al, 2003. Endothelial recovery: The next target in restenosis prevention. Circulation, vol. 107:2635-2637.*
Sheppard and Eisenberg, 2001. Editorial: Intracoronary radiotherapy for restenosis. New England Journal of Medicine, vol. 344(4):295-297.*
Grube et al ("Rapamycin Analogs for Stent-based local drug delivery," Herz 2004; 29:162-6.*
Grube et al "Rapamycin Analogs for Stent-based local drug delivery," Herz 2004; 29:162-6.*
U.S. Appl. No. 10/816,072, filed Mar. 31, 2004, Dugan et al.

* cited by examiner

*Primary Examiner* — Suzanne Ziska
(74) *Attorney, Agent, or Firm* — Squire Sanders (US) LLP

(57) ABSTRACT

Provided herein are coating comprising PEA-TEMPO/PEA-BZ for implantable medical devices, the coating being useful for the controlled delivery of bioactive agents into a patient's body.

10 Claims, 1 Drawing Sheet

PEA-TEMPO/PEA-BZ COATINGS FOR CONTROLLED DELIVERY OF DRUG FROM IMPLANTABLE MEDICAL DEVICES

FIELD

This invention relates to the fields of polymer chemistry, materials science and medical devices. In particular it relates to coatings useful for the controlled delivery of bioactive agents from implantable medical devices.

BACKGROUND

Co-poly-{[N,N'-sebacoyl-bis-(L-leucine)-1,6-hexylene-diester]-[N,N'-sebacoyl-L-lysine benzyl ester]}(PEA-BZ) and co-poly-{[N,N'-sebacoyl-bis-(L-leucine)-1,6-hexylene diester]-[N,N'-sebacoyl-L-lysine 4-amino-TEMPO amide]} (PEA-TEMPO)) are polymers known to be useful as bioactive agent (BA) delivery coatings for implantable medical devices (IMDs). It can be difficult, however, to obtain a desired BA release profile from coatings comprising these polymers while maintaining the overall stability and mechanical strength required of an IMD coating. This is due in part to the low glass transition temperatures ($T_g$) of PEA-BZ and PEA-TEMPO, approximately 23° C. and 33° C. Low $T_g$s, however, can be a mixed blessing: a low Tg is usually associated with high permeability and high permeability can be an asset when dealing with the stringent requirements of the FDA CDER whereby the dosage delivered by controlled release from an implantable device must equal at least 80% of the dose delivered by conventional means. On the other hand, high permeability can make long-term sustained release difficult since the BA may elute too rapidly from the coating.

What is needed are PEA-BZ/PEA-TEMPO coatings that exhibit optimal balance among parameters such as, without limitation, release rate, permeability, mechanical strength and stability so as to be able to achieve any desired release profile. The present invention provides such coatings.

SUMMARY

Thus, an aspect of this invention is a coating for an implantable medical device, comprising:
a first layer disposed over a surface of the implantable medical device, comprising a bioactive agent;
a second release profile controlling layer disposed over the first layer comprising poly{[N,N'-sebacoyl-bis-(L-leucine)-1,6-hexylene diester]-co-[N,N'-sebacoyl-L-lysine 4-amino-2,2,6,6-tetramethylpiperidine-N-oxide]}(PEA-TEMPO) and poly{[N,N'-sebacoyl-bis-(L-leucine)-1,6-hexylene diester]-co-[N,N'-sebacoyl-L-lysine benzyl ester]}(PEA-BZ), wherein the molar ratio of PEA-TEMPO to PEA-BZ is from 0:1 to 1:0; wherein:
bioactive agent loading in the first layer is about 50 µg/cm² to about 250 µg/Cm²;
bioactive agent loading in the second layer is about 0 µg/cm² to about 50 µg/cm²; and,
PEA-TEMPO/PEA-BZ loading in the second layer is about 100 µg/cm² to about 2500 µg/cm².

In an aspect of this invention, the coating further comprises PEA-TEMPO/PEA-BZ in the first layer at a loading of about 150 µg/cm² to about 2200 µg/cm², wherein the wt:wt ratio of PEA-TEMPO/PEA-BZ to bioactive agent is from about 3:1 to about 20:1.

In an aspect of this invention, the coating further comprises a topcoat layer disposed over the second layer.

In an aspect of this invention, the topcoat further comprises an biobenefical material.

In an aspect of this invention the bioactive agent is selected from the group consisting of paclitaxel, docetaxel, estradiol, nitric oxide donors, super oxide dismutases, super oxide dismutases mimics, 4-amino-2,2,6,6-tetramethylpiperidine-1-oxyl(4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, progenitor cell capturing antibody, prodrugs of any of the preceding and combinations of any of the preceding.

In an aspect of this invention, the bioactive agent is everolimus.

In an aspect of this invention, everolimus loading in the first layer is about 70 µg/cm² to about 150 µg/cm².

In an aspect of this invention, everolimus loading in the first layer is about 90 µg/cm² to about 110 µg/cm².

In an aspect of this invention, the first layer further comprises PEA-TEMPO/PEA-BZ, wherein the wt:wt ratio of PEA-TEMPO/PEA-BZ to everolimus is about 5:1 to about 15:1.

In an aspect of this invention, the wt:wt ratio of PEA-TEMPO/PEA-BZ to everolimus is about 6:1 to about 10:1.

In an aspect of this invention:
about 15 wt % to about 20 wt % of the everolimus is released from the coating over about a 1 day period;
about 26 wt % to about 31 wt % of the everolimus is released from the coating over about a 3 day period;
about 40 wt % to about 48 wt % of the everolimus is released from the coating over about a 7 day period;
about 56 wt % to about 67 wt % of the everolimus is released from the coating over about a 14 day period; and,
about 80 wt % to about 95 wt % of the everolimus is released from the coating over about a 28 day period.

In an aspect of this invention, the bioactive agent loading in the first layer is about 49 µg/cm² to about 200 µg/cm² and its loading in the second layer is about 1 µg/cm² to about 50 µg/cm².

An aspect of this invention is a method for the treatment or prevention of restenosis comprising implanting in a patient in need thereof a stent having a coating comprising everolimus as set forth above.

DETAILED DESCRIPTION

DISCUSSION

Figure 1:
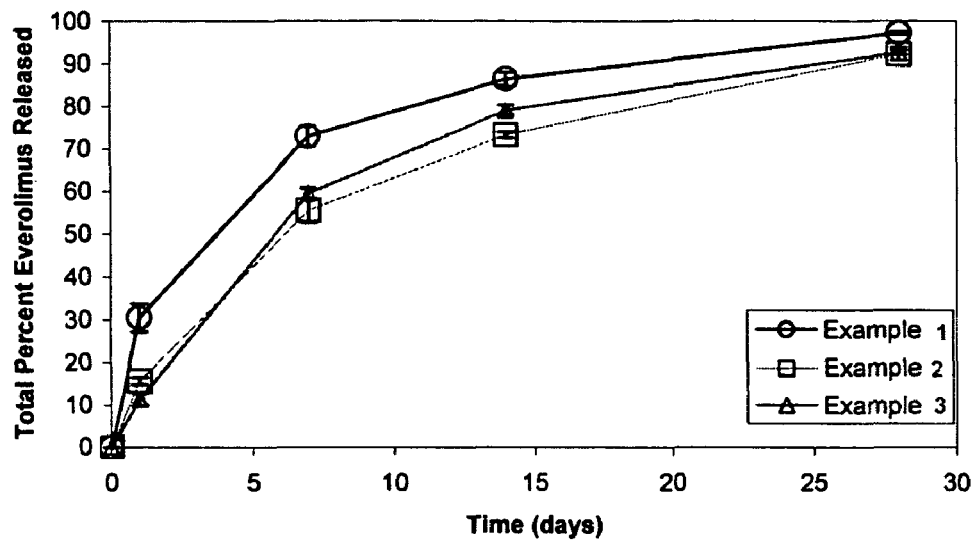
FIG. 1 shows the in vivo release profiles of everolimus from three coatings of this invention.

PEA-TEMPO and PEA-BZ are versatile polymers useful as BA-delivery coatings for IMDs. Provided herein are PEA-TEMPO/PEA-BZ coatings for IMDs that exhibit a beneficial balance of release profile, permeability, loading, mechanical strength and stability. That is, the coatings are capable of fast release, intermediate sustained release or sustained release of a BA while maintaining good physical stability and mechanical strength.

As used herein, "PEA-TEMPO/PEA-BZ" means that PEA-TEMPO may be present alone in whatever application is being discussed or PEA-BZ may be present alone or a blend of PEA-TEMPO and PEA-BZ may be present.

The coatings herein may contain a single BA or a mixture of BAs so long as the coating parameters described herein are met. They may even contain one or more additional biocompatible/biodegradable or biocompatible/non-biodegradable polymer(s) so long as the additional polymers do not detrimentally affect the balance of physical characteristics achieved by the coatings of this invention.

As used herein, "bioactive agent" refers any substance that can be used for therapeutic, prophylactic, or diagnostic purposes. A therapeutic purpose refers to the treatment of an on-going disease or disorder, the goal being to cure it or at least ameliorate its symptoms. A prophylactic purpose refers to the administration of a BA before any disease or disorder has manifested itself or to administration after the disease or disorder has been subjected to therapeutic treatment to prevent recurrence of the disease or disorder or of symptoms of the disease or disorder. A BA may be, without limitation, anti-proliferative, anti-inflammmatory, antineoplastic, anti-platelet, anti-coagulant, anti-fibrin, antithrombonic, antimitotic, antibiotic, antiallergic, antioxidant and/or cystostatic. Examples of BAs include, without limitation, natural products such as antibiotics, modified natural products, synthetic inorganic and organic drugs, proteins, peptides, polysaccharides and other sugars, lipids and DNA or RNA nucleic acid sequences. Nucleic acid sequences include, without limitation, genes, antisense oligo and polynucleotides and ribozymes. Other BAs include, again without limitation, antibodies, receptor ligands, enzymes, adhesion peptides, blood clotting factors, blood clot dissolving agents such as streptokinase and tissue plasminogen activator, antigens for immunization, hormones and growth factors and retroviral vectors for use in gene therapy. Specific examples of BAs include, without limitation, anti-proliferative agents such as rapamycin, methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin, 40-O-(2-hydroxy)ethylrapamycin(everolimus), paclitaxel and docetaxel. Examples of antineoplastics and antimitotics include methotrexate, azathioprine, vincristine, vinblastine, fluorouracil, doxorubicin hydrochloride, and mitomycin. Examples of antiplatelet compounds, anticoagulants, antifibrin, and antithrombins include sodium heparin, low molecular weight heparins, heparinoids, hirudin, argatroban, forskolin, vapiprost, prostacyclin, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä, calcium channel blockers such as nifedipine, colchicine, fibroblast growth factor (FGF) antagonists, fish oil (omega 3-fatty acid), histamine antagonists, lovastatin (an inhibitor of HMG-CoA reductase), a cholesterol lowering drug, monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as vitamins, and combinations thereof. Examples of anti-inflammatory agents include, without limitation, steroidal and non-steroidal anti-inflammatory agents, tacrolimus, dexamethasone and clobetasol. Examples of cytostatic agents include, without limitation, angiopeptin, angiotensin converting enzyme inhibitors such as captopril, cilazapril or lisinopril. An example of an antiallergic agent is permirolast potassium. Other BAs that may be used with a coating of this invention include alpha-interferon, RGD peptides, and genetically engineered epithelial cells. The foregoing substances may also used as their corresponding pro-drugs. Other BAs that are currently available or that may be developed in the future are equally usable with the coatings herein.

A presently preferred BA for use with the coatings of this invention is everolimus.

As used herein, BA also include biobeneficial materials (BMs). As used herein, BMs differ from BAs in that BAs must be released from a coating to have a therapeutic or prophylactic effect while BMs have an effect while remaining substantially within the coating. By "substantially" is meant that, while some of the BM may leak out of a coating, release from the coating is not necessary (although it is not necessarily detrimental) for it to have its beneficial effect. BMs are in general non-toxic, non-antigenic, non-immunogenic substances that enhance the biocompatibility of an IMD by being non-fouling, hemocompatible, actively non-thrombogenic and/or anti-inflammatory.

Representative biobeneficial materials include, but are not limited to, polyethers such as poly(ethylene glycol), copoly (ether-esters) (e.g. PEO/PLA); polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, and combinations thereof.

A presently preferred biobeneficial material is a polyether such as poly(ethylene glycol) (PEG) or polyalkylene oxide.

Any manner of IMD can be coated with a drug-containing polymer of this invention. As used herein an IMD refers to any type of appliance that is totally or partly introduced, surgically or medically, into a patient's body or by medical intervention into a natural orifice, and which is intended to remain there after the procedure. As used herein, patient refers to either a medical or veterinary patient. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, self-expandable stents, balloon-expandable stents, stent-grafts, grafts, artificial heart valves and cerebrospinal fluid shunts.

IMDs of constructed of virtually any biocompatible material, as such are presently known or as such may be developed in the future, may be used with a coating of this invention. For example, without limitation, an IMD useful with a coating of this invention may be made of one or more biocompatible metals or alloys thereof including, but not limited to, cobalt-chromium alloy (ELGILOY, L-605), cobalt-nickel alloy (MP-35N), 316L stainless steel, high nitrogen stainless steel, e.g., BIODUR 108, nickel-titanium alloy (NITINOL), tantalum, platinum, platinum-iridium alloy, gold and combinations thereof.

IMD suitable for use with the coatings herein may also be made of polymers that are biocompatible and biostable or biodegradable, the latter term including bioabsorbable and/or bioerodable.

Among useful biocompatible, relatively biostable polymers are, without limitation polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers include naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

One or more synthetic or semi-synthetic biocompatible, biodegradable polymers may also be used to fabricate an IMD useful with this invention. AS used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyhydroxyacids, polyhydroxyalkanoates, polyanhydrides, polyesters, polyorthoesters, polyamino acids, polyoxymethylenes, poly(ester-amides) and polyimides.

Blends and copolymers of the above polymers may also be used and are within the scope of this invention. Based on the disclosures herein, those skilled in the art will recognize those IMDs and those materials from which they may be fabricated that will be useful with the coatings of this invention.

At present, preferred IMDs for use with the coatings of this invention are stents. A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of BAs to specific sites in a patient's body. In fact, BA delivery may be the sole purpose of the stent. Often, however, a stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. In any event, due to the expansion of the stent, any coating thereon must be flexible and capable of elongation. PEA-TEMPO/PEA-BZ coatings of this invention exhibit these characteristics.

As mentioned above, the PEA-TEMPO/PEA-BZ coatings herein are capable of fast, intermediate sustained or sustained release of BAs.

As used herein, "fast release" refers to elution of about 80% to about 99.5% of a drug from a coating on an implantable medical device within about 1 to about 3 days following implantation.

As used herein, "intermediate sustained release" refers to elution of about 80% to about 99.5% of a drug from a coating on an implantable medical device over about 3 to about 28 days wherein the concentration of the drug reaches a therapeutic level within about the first day and is maintained at that level until the total amount eluted is at least 80%.

As used herein, "sustained release" refers to elution of about 80% to about 99.5% of a drug from a coating on an implantable medical device over about 28 or more days wherein the concentration of the drug reaches a therapeutic level within the first about 1 to about 3 days and is maintained at that level until the total amount eluted is at least 80%.

As used herein, the word "about," wherever it is used herein, means that the parameter modified by the word may vary by ±20% and still be within the scope of this invention.

One of the factors affecting release profile is loading, that is the quantity of a material present in a particular coating. As used herein, loading applies to both BAs and polymers. Loading is expressed as a weight of material per unit area, e.g., $\mu g/cm^2$. Thus, in a non-limiting example, if a 12 mm VISION stent (Guidant Corporation), which has a surface area of 0.5556 $cm^2$, is coated with a uniform layer comprising 100 µg of a BA, the loading of the BA on the stent would be 179.9 $\mu g/cm^2$. All loading in this application are determined by a similar calculation whether BAs or polymers are the subject of the loading.

As used herein, "release profile" refers to the amount of BA released from a coating as a function of time. To achieve the range of release profiles described above, the loading of a BA will be from about 25 $\mu g/cm^2$ to about 250 $\mu g/cm^2$, with different BAs having different preferred ranges readily ascertainable based on the disclosures here. For example, for everolimus, the loading is preferably from about 70 $\mu g/cm^2$ to about 150 $\mu g/cm^2$ and presently most preferably from about 90 $\mu g/cm^2$ to about 110 $\mu g/cm^2$. If more than one BA is employed in the coating, each will have its own preferred loading but for the purposes of this invention the total loading of all BAs should be within the aforesaid maximum range.

Also affecting release profile is the loading of PEA-TEMPO/PEA-BZ on the IMD. As stated previously, the goal is to achieve desirable release profiles while maintaining optimal coating characteristics with regard to permeability, stability and mechanical strength so that the target release profile can be achieved while the coating retains the physical characteristics to withstand the forces that may develop during deployment of the IMD such as, in the case of stents, crimping and expansion. The loading of PEA-TEMPO/PEA-BZ in the coatings of this invention will range from about 150 µg/cm² to about 2200 µg/cm², preferably from about 700 µg/cm² to about 1800 µg/cm² and presently most preferably from about 1400 µg/cm² to about 1800 µg/cm².

A third factor affecting the release profile of a BA from a coating of this invention is the weight to weight (wt:wt) ratio of total polymer to total BA in the coating. The wt:wt ratio of PEA-TEMPO/PEA-BZ to BA in coatings of this invention ranges from about 3:1 to about 20:1, preferably from about 5:1 to about 15:1, and presently most preferably, from about 6:1 to about 10:1. If more than one BA is present in the coating, the ratio is selected based on the characteristics of the BA having the most stringent release profile requirements. As a non-limiting example, if everolimus is the key BA to be released, the presently preferred wt:wt ratio of total polymer to everolimus is presently most preferably from about 6:1 to about 10:1, depending on the release profile desired, fast, intermediate sustained or sustained. Any other BAs that might be included in the coating would have a release profile dictated by the parameters selected for everolimus. In some cases the parameters, while remaining within the above-described ranges, might be modified to values intermediate between the optimum for each individual BA to achieve an overall acceptable average release profile.

Using the preceding parameters and the disclosures herein, a release profile from fast to intermediate sustained to sustained can be achieved.

The PEA-TEMPO/PEA-BZ coatings of this invention can be disposed over an IMD in various ways. As used herein, "disposed over" means that the coating is placed essentially uniformly over the target region of the surface of the IMD. While "applied to" has generally the same meaning as "disposed over," the latter infers that there may be something else, such as, without limitation, another layer of material, between the coating layers or between a coating layer and the surface of the IMD whereas the former infers that the coating is placed directly onto the other coating or onto the surface of the IMD. The simplest method of disposing a coating over an IMD, if the IMD is known or found to adhere satisfactorily to PEA-TEMPO/PEA-BZ, is to formulate a single coating containing the BA (and any other substances such as BMs) and PEA-TEMPO/PEA-BZ using the above disclosure to determine the proper combination of parameters to achieve the desired release profile and apply it directly to the bare surface of the IMD as a single layer. A BA-containing polmer layer is referred to in the art as a "reservoir layer."

An alternative construct comprises applying a primer layer between the reservoir layer and the surface of the IMD to effect or improve adhesion of the reservoir layer to the surface of the IMD.

Yet another construct comprises applying a reservoir layer directly to the bare surface of the IMD or atop a previously applied primer layer and then applying a second layer atop the reservoir layer. In this construct, the second layer becomes the primary release profile controlling layer. The second layer may be directly in contact with the external environment or it may be over-coated with a topcoat layer. Generally, the topcoat layer is a thin layer intended simply to protect the underlying layers from contact with the environment until the IMD has been implanted at a target location. That is, the topcoat layer does not participate in establishing a release profile If desired, however, the topcoat layer may contain BMs to improve the biocompatibility and performance of the IMD. In either case, if used, a topcoat is selected that either rapidly disintegrates under physiological conditions or is sufficiently permeable as to be virtually transparent to the BA being delivered.

The controlling characteristics of the release profile controlling second layer are its loading and its $T_g$. The $T_g$ of the coating will depend on the molar ratio of PEA-TEMPO to PEA-BZ in the layer. As noted previously, the $T_g$ of PEA-TEMPO is about 33° C. and that of PEA-BZ is about 23° C. Thus to achieve a slower release rate a higher proportion of PEA-TEMPO would be used. On the other hand, to achieve the fastest release PEA-BZ alone would be used. To achieve intermediate release rates, a blend of PEA-TEMPO and PEA-BZ would be used since the $T_g$ of a miscible blend of polymers is roughly linear with the molar ratio of the component polymers. By adjusting the ratio of PEA-TEMPO to PEA-BZ in the second layer, release rates ranging from rapid release to intermediate sustained release to sustained release can be achieved.

The loading of PEA-TEMPO/PEA-BZ in the second layer will be from about 100 µg/cm² to about 2500 µg/cm², preferably from about 350 µg/cm² to about 1500 µg/cm² and presently most preferably, from about 500 µg/cm² to about 1100 µg/cm², depending on the desired release profile.

The ratio of PEA-TEMPO to PEA-BZ in the reservoir layer may also participate in determining the over-all release rate since a drug must elute from the first layer into the second layer before it can be released. In general it is preferred that, when a release profile layer controlling layer is used, the reservoir layer have a fast release profile so that the second layer will in fact control the actual release profile. If a second layer, however, cannot be formulated that will provide a desired release profile without detrimentally affecting the mechanical strength and stability of the coating as a whole, the composition of the first layer can be modified in the same manner as the second layer as an additional means of controlling the release profile.

In some instances a release that is at first very rapid, i.e., essentially a "burst" as described above, may be desirable in which case the drug may be apportioned between the reservoir (first) layer and the rate-controlling (second) layer. About 1 µg/cm² to about 50 µg/cm² of a BA may be contained in the second layer. The BA in the second layer will be released into the environment very shortly after exposure of the second layer to the physiological environment; that is in a much shorter time span even than that described above as "fast release." A topcoat may be provided to protect the BA-containing second layer.

A further coating construct of this invention would be to first apply a primer layer to the bare surface of an IMD, which primer layer may comprise PEA-TEMPO/PEA-BZ or a different primer known to, or as such may become known to, those skilled in the art. Next a neat layer of BA is applied directly atop the primer. As used herein, "neat" means that no reservoir layer-forming or release profile controlling polymer (s) are included in the layer. In this construct, the second layer is totally responsible for the release profile of the coating.

The dosage of BA to be delivered will depend on factors such as, without limitation, the condition of the patient; the nature and progression of the disease or disorder; the nature of the therapy, i.e., therapeutic or prophylactic, the expected residence time of the bioactive agent at the target site (that is, its decomposition rate in vivo), the nature and type of other BAs in the formulation, etc. Those skilled in the art will readily be able to determine therapeutic and/or prophylactic effective dosages from the literature or by empirical studies using appropriate animal models. Such procedures are well-known to those skilled in the art and are not addressed here.

In particular at present a coating herein may be disposed on a stent and the stent may be implanted to treat or prevent restenosis. By "treat" is meant that restenosis is already detected in a patient and the everolimus-coated stent is implanted at the site of restenosis to retard the progress of the restenosis, that is, to slow the closure of the lumen of the vascular entity being treated. In this context, treatment also includes prophylaxis in that it may delay the onset of restenosis; that is, an everolimus-coated stent is implanted in a patient before restenosis is observed in an effort to maintain the patency of the vascular entity being treated as long as possible. By "prevent" is meant to put off restenosis of the vascular entity for the remaining life-span of the patient, another example of prophylaxis.

EXAMPLES

The examples presented in this section are provided by way of illustration of the current invention only and are not intended nor are they to be construed as limiting the scope of this invention in any manner whatsoever. Each of the examples the follows relates to the coating of a 12 mm VISION (Guidant Corporation) stent, which has a coatable surface area of 0.5556 cm$^2$.

Example 1

About a 2% (w/w) solution of PEA-BZ in absolute ethanol was prepared. Everolimus was added at a BA(solids):PEA-BZ(solution) w:w ratio of about 1:500, which corresponds to a BA(solids):PEA-BZ(solids) w:w ratio of about 1:10.

The solution was then sprayed using a 0.014 fan nozzle with a feed pressure of about 0.2 atm and an atomization pressure of about 1.3 atm onto the surface of a bare VISION stent and dried to form a first layer. About 20 μg of solution was applied per pass; each pass being dried at about 62° C. for about 10 seconds before a subsequent pass was applied. When the desired amount of solution was applied to the IMD, the IMD was warmed to about 50° C. for about 1 hour to form the reservoir layer. The reservoir layer comprised of about 560 μg of PEA-BZ and about 56 μg of everolimus. A topcoat layer was then applied over the reservoir layer using the PEA-BZ solution without added everolimus and the same coating technique just described. The topcoat layer contained about 384 μg of PEA-BZ.

Example 2

About a 2% (w/w) solution of PEA-TEMPO in absolute ethanol was prepared. Everolimus was added at a BA(solids):PEA-TEMPO(solution) w:w ratio of about 1:300, which corresponds to a BA(solids):PEA-TEMPO (solids) ratio of about 1:6.

The solution was then sprayed onto the surface of a bare VISION stent using a 0.014 fan nozzle, a feed pressure of about 0.2 atm, and an atomization pressure of about 1.3 atm. About 20 μg of wet coating was applied per pass, each pass being dried at about 62° C. for about 10 seconds before the next pass. After the last pass, the layer was dried at about 50° C. for about 1 hour to give a dry reservoir layer containing about 336 μg of PEA-TEMPO and about 56 μg of everolimus. A reservoir layer comprised of the solution without added everolimus was applied over the reservoir layer using the same coating procedure just describe with regard to the reservoir layer until about 400 μg of PEA-TEMPO was applied.

Example 3

About a 2% (wt:wt) solution of PEA-TEMPO in absolute ethanol was prepared. A separate 2% (wt:wt) solution of everolimus in absolute ethanol was also prepared.

The PEA-TEMPO solution was sprayed onto the bare surface of a VISION stent using a 0.014 fan nozzle, a feed pressure of about 0.2 atm, and an atomization pressure of about 1.3 atm. About 20 μg of wet coating was applied per pass; each pass being dried at about 62° C. for about 10 seconds before the next pass. After the last pass, the coating was dried at about 50° C. for about 1 hour to provide a dry primer layer comprising about 75 μg PEA-TEMPO. A neat layer of everolimus was then applied using the same coating procedure just described until about 56 μg of everolimus was applied. A topcoat layer was then applied using the 2% PEA-TEMPO solution and the same coating procedure until about 600 μg of PEA-TEMPO had been applied.

Example 4

Figure 2:
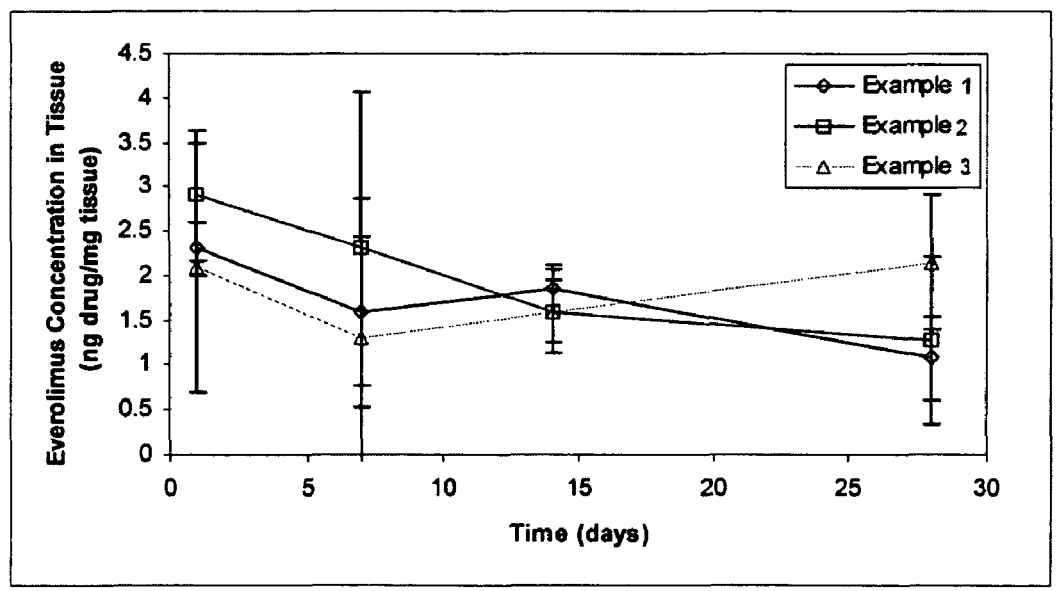
FIG. 2 shows everolimus concentrations in tissues in which stents comprising the above coatings were implanted.

The above stents were implanted in the coronary arteries (LCX, LAD, and RCA) and in the internal mammary arteries (RIMA and LIMA) of porcine animal models to determine the release profile and tissue concentrations of everolimus at 1, 7, 14, and 28 days post-implant. The IMDs of examples 2 and 3 exhibited sustained release of everolimus, while the IMD of Example 1 exhibited intermediate sustained release (FIG. 1). In spite of the differences in release kinetics, the everolimus concentration in the stented tissue was equivalent for all three IMDs (FIG. 2).

While particular non-limiting embodiments of the present invention have been described, changes and modifications will become apparent to those skilled in the art based on the disclosures herein. All such changes and modifications are within the scope of this invention.

What is claimed:

1. A coating for an implantable medical device, comprising:
   a first layer disposed over a surface of the implantable medical device, comprising poly{[N,N'-sebacoyl-bis-(L-leucine)-1,6-hexylene diester]-co-[N,N'-sebacoyl-L-lysine 4-amino-2,2,6,6-tetramethylpiperidine-N-oxide]}(PEA-TEMPO) and poly {[N,N'-sebacoyl-bis-(L-leucine)-1,6-hexylene diester]-co-[N,N'-sebacoyl-L-lysine benzyl ester]}(PEA-BZ) and a bioactive agent;
   wherein
      bioactive agent loading in the first layer is about 49 μg/cm$^2$ to about 250 μg/cm$_2$,
      PEA-TEMPO/PEA-BZ loading in the first layer is about 150 μg/cm$^2$ to about 2200 μg/cm$^2$, and
      the wt:wt ratio of PEA-TEMPO/PEA-BZ to bioactive agent is about 3:1 to about 20:1,
   a second release profile controlling layer disposed over the first layer comprising poly {[N,N'-sebacoyl-bis-(L-leucine)-1,6-hexylene diester]-co-[N,N'-sebacoyl-L-lysine 4-amino-2,2,6,6-tetramethylpiperidine-N-oxide]} (PEA-TEMPO) and poly {[N,N'-sebacoyl-bis-(L-leucine)-1,6-hexylene diester]-co-[N,N'-sebacoyl-L-lysine benzyl ester]}(PEA-BZ) and a bioactive agent;
   wherein:
      bioactive agent loading in the second layer is about 0 μg/cm$^2$ to about 50 μg/cm$^2$; and
      PEA-TEMPO/PEA-BZ loading in the second layer is about 100 μg/cm$^2$ to about 2500 μg/cm$^2$,
   a topcoat layer disposed over the second layer, wherein the topcoat comprises an biobenefical material selected from the group consisting of poly(propylene oxide), poly (ethylene glycol) acrylate (PEGA), phosphoryl choline, choline, poly(aspirin), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), polypropylene oxide-co-polyethylene glycol, poly(tetramethylene glycol), hydroxy functional poly(vinyl pyrrolidone), fibrinogen, dextran, dextrin, heparin, fragments and derivatives of heparin, glycosamino glycan (GAG), GAG derivatives, elastin, chitosan, alginate, hydroxyethyl methacrylate (HEMA), hydroxypropyl methacrylate (HPMA), hydroxypropylmethacrylamide, methacrylic acid (MA) and acrylic acid (AA).

2. The coating of claim 1, wherein the bioactive agent is selected from the group consisting of paclitaxel, docetaxel, estradiol, nitric oxide donors, super oxide dismutases, super oxide dismutases mimics, 4-amino-2,2,6,6-tetramethylpiperidine-1oxyl (4-amino-TEMPO), tacrolimus, dexamethasone, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, progenitor cell capturing antibody, prodrugs of any of the preceding and combinations of any of the preceding.

3. The coating of claim 2, wherein in the bioactive agent is everolimus.

4. The coating of claim 3, wherein everolimus loading in the first layer is about 70 μg/cm$^2$ to about 150 μg/cm$^2$.

5. The coating of claim 4, wherein everolimus loading in the first layer is about 90 μg/cm$^2$ to about 110 μg/cm$^2$.

6. The coating of claim 5, wherein the wt:wt ratio of PEA-TEMPO/PEA-BZ to everolimus is about 5:1 to about 15:1 in the first layer.

7. The coating of claim 6, wherein the wt:wt ratio of PEA-TEMPO/PEA-BZ to everolimus is about 6:1 to about 10:1.

8. The coating of claim 7, wherein:
about 15 wt % to about 20 wt % of the everolimus is released from the coating over about a 1 day period;
about 26 wt % to about 31 wt % of the everolimus is released from the coating over about a 3 day period;
about 40 wt % to about 48 wt % of the everolimus is released from the coating over about a 7 day period;
about 56 wt % to about 67 wt % of the everolimus is released from the coating over about a 14 day period; and, about 80 wt % to about 95 wt % of the everolimus is released from the coating over about a 28 day period.

9. The coating of claim 1, wherein the bioactive agent loading in the first layer is about 49 μg/cm$^2$ to about 200 μg/cm$^2$ and its loading in the second layer is about 1 μg/cm$^2$ to about 50 μg/cm$^2$.

10. A method for the treatment of restenosis comprising implanting in a patient in need thereof a stent having the coating set forth in claim 3.

* * * * *